US010420682B2

United States Patent
Lindström et al.

(10) Patent No.: US 10,420,682 B2
(45) Date of Patent: Sep. 24, 2019

(54) SENSOR ARRANGEMENT FOR MEASURING MOISTURE AND THE PRESENCE OF A PERSON ON A BASE

(71) Applicant: MARICARE OY, Vantaa (FI)

(72) Inventors: Juha Lindström, Espoo (FI); Atte Piipponen, Kerava (FI); Göran Sundholm, Tuusula (FI)

(73) Assignee: MARICARE OY, Vantaa (FI)

( * ) Notice: Subject to any disclaimer, the term of this patent is extended or adjusted under 35 U.S.C. 154(b) by 238 days.

(21) Appl. No.: 15/325,182

(22) PCT Filed: Jun. 23, 2015

(86) PCT No.: PCT/FI2015/050459
§ 371 (c)(1),
(2) Date: Jan. 10, 2017

(87) PCT Pub. No.: WO2016/009109
PCT Pub. Date: Jan. 21, 2016

(65) Prior Publication Data
US 2017/0172813 A1    Jun. 22, 2017

(30) Foreign Application Priority Data
Jul. 18, 2014    (FI) .................................. 20145680

(51) Int. Cl.
*A61F 13/42*    (2006.01)
*G08B 21/20*    (2006.01)
(Continued)

(52) U.S. Cl.
CPC ............ *A61F 13/42* (2013.01); *A61B 5/0002* (2013.01); *A61B 5/1115* (2013.01); *A61B 5/202* (2013.01);
(Continued)

(58) Field of Classification Search
None
See application file for complete search history.

(56) References Cited

U.S. PATENT DOCUMENTS 5,144,284 A *    9/1992    Hammett .............. A61B 5/1115
                                                    128/886
5,269,030 A *   12/1993    Pahno ................... A61G 7/0005
                                                    4/480
(Continued)

FOREIGN PATENT DOCUMENTS

CN    101007525 A      8/2007
EP    2 548 473 A2     1/2013
(Continued)

OTHER PUBLICATIONS

International Search Report for PCT/FI2015/050459 (PCT/ISA/210) dated Oct. 7, 2015.
(Continued)

*Primary Examiner* — Steven Lim
*Assistant Examiner* — Muhammad Adnan
(74) *Attorney, Agent, or Firm* — Birch, Stewart, Kolasch & Birch, LLP (57) ABSTRACT

Sensor arrangement and method for monitoring a person with a sensor arrangement, which includes measuring electronics and a sensor structure that can be fitted onto a base. The sensor structure includes at least one sensor, and the arrangement determines, by the data measured by the measuring electronics and the sensor, a change in the moisture of the base and the presence of a person on the base.

23 Claims, 3 Drawing Sheets

(51) Int. Cl.

| | | |
|---|---|---|
| *G08B 21/22* | (2006.01) | |
| *G08B 25/08* | (2006.01) | |
| *G01L 9/00* | (2006.01) | |
| *G01L 19/00* | (2006.01) | |
| *G01L 1/14* | (2006.01) | |
| *G01L 1/16* | (2006.01) | |
| *G01L 1/18* | (2006.01) | |
| *G01L 1/22* | (2006.01) | |
| *A61B 5/11* | (2006.01) | |
| *A61B 5/20* | (2006.01) | |
| *A61B 5/00* | (2006.01) | |
| *G01N 27/04* | (2006.01) | |
| *G01N 27/22* | (2006.01) | |
| *A61B 90/00* | (2016.01) | |

(52) U.S. Cl.
CPC ........... *A61B 5/4266* (2013.01); *A61B 5/447* (2013.01); *A61B 5/6891* (2013.01); *A61B 5/6892* (2013.01); *G01L 1/14* (2013.01); *G01L 1/16* (2013.01); *G01L 1/18* (2013.01); *G01L 1/22* (2013.01); *G01L 9/0005* (2013.01); *G01L 19/0092* (2013.01); *G01N 27/048* (2013.01); *G01N 27/223* (2013.01); *G08B 21/20* (2013.01); *G08B 21/22* (2013.01); *G08B 25/08* (2013.01); *A61B 2090/064* (2016.02); *A61B 2560/0242* (2013.01); *A61B 2562/029* (2013.01); *A61B 2562/0247* (2013.01); *A61B 2562/0261* (2013.01)

(56) References Cited

U.S. PATENT DOCUMENTS

| 5,459,452 | A  * | 10/1995 | DePonte ............. A61F 13/42 |
| | | | 128/886 |
| 5,801,307 | A  * | 9/1998  | Netzer ............. B32B 17/10036 |
| | | | 73/170.17 |
| 8,191,187 | B2   | 6/2012  | Brykalski ........... A47C 21/044 |
| | | | 5/423 |
| 8,884,769 | B2 * | 11/2014 | Novak .................. A61F 13/42 |
| | | | 340/540 |
| 9,192,532 | B2 * | 11/2015 | Primo ................... A47C 7/744 |
| 9,277,882 | B2 * | 3/2016  | Eilebrecht ........... A61B 5/6891 |
| 9,649,230 | B1 * | 5/2017  | Li ......................... A61F 13/42 |
| 9,974,463 | B2 * | 5/2018  | Rutkove ............... A61B 5/4519 |
| 10,022,277 | B2 * | 7/2018 | Heil ...................... A61F 13/42 |
| 10,104,982 | B2 * | 10/2018 | Alletto ............... A47C 21/042 |
| 10,265,231 | B2 * | 4/2019 | O'Reagan ............. A61G 7/057 |
| 2004/0199318 | A1 | 10/2004 | Shieh et al. |
| 2005/0159685 | A1 * | 7/2005 | Klein ..................... A61H 23/02 |
| | | | 601/49 |
| 2006/0187038 | A1 * | 8/2006 | Shieh ....................... G01B 7/14 |
| | | | 340/562 |
| 2008/0300559 | A1 * | 12/2008 | Gustafson ............... A61F 13/42 |
| | | | 604/361 |
| 2010/0073181 | A1 * | 3/2010 | Ootaka .................... B60N 2/00 |
| | | | 340/667 |
| 2010/0231023 | A1 * | 9/2010 | Wuerstlein ............. B60N 2/002 |
| | | | 297/410 |
| 2010/0241094 | A1 * | 9/2010 | Sherron ................... A61F 13/42 |
| | | | 604/361 |
| 2010/0308846 | A1 * | 12/2010 | Camus ..................... G01L 1/142 |
| | | | 324/679 |
| 2011/0004435 | A1 * | 1/2011 | Lindstrom ........... G08B 21/043 |
| | | | 702/138 |
| 2011/0115635 | A1 * | 5/2011 | Petrovski ............. A47C 21/044 |
| | | | 340/584 |
| 2011/0302719 | A1 | 12/2011 | Schwirian et al. |
| 2012/0161953 | A1 * | 6/2012 | Nakagawa ............. B60N 2/002 |
| | | | 340/438 |
| 2013/0019405 | A1 | 1/2013 | Flanagan et al. |
| 2013/0191057 | A1 * | 7/2013 | Ben Shalom .......... A61B 5/103 |
| | | | 702/64 |
| 2014/0039351 | A1 * | 2/2014 | Mix ....................... A61B 5/1114 |
| | | | 600/587 |
| 2014/0340230 | A1 * | 11/2014 | Flanagan ............... A61G 7/057 |
| | | | 340/604 |

FOREIGN PATENT DOCUMENTS

| JP | 2007-333548 A | 12/2007 |
| JP | 2009-156641 A | 7/2009 |
| JP | 2010-510832 A | 4/2010 |
| JP | 2011-122972 A | 6/2011 |
| JP | 2012-141137 A | 7/2012 |

OTHER PUBLICATIONS

Written Opinion of the International Searching Authority for PCT/FI2015/050459 (PCT/ISA/237) dated Oct. 7, 2015.
Chinese Office Action and Search Report for Chinese Application No. 201580037553.7, dated Nov. 19, 2018, with English translation.
English translation of the Japanese Notification of Reasons for Refusal for Japanese Application No. 2017-501369, dated Nov. 27, 2018.

* cited by examiner

SENSOR ARRANGEMENT FOR MEASURING MOISTURE AND THE PRESENCE OF A PERSON ON A BASE

FIELD OF THE INVENTION

The invention relates to a sensor arrangement and to a method, which in particular can be used for monitoring a person on a base.

BACKGROUND OF THE INVENTION

The monitoring of the condition of elderly people in various environments is indispensable if it is desired to respond to the growing proportion of the population that is ageing. Presented in the art are various means for monitoring sick people or other people needing care, both in home surroundings and in institutional care. For example, over the course of time many types of monitoring means have been used in hospitals for arranging the monitoring of patients.

Bed sensors form one type of sensor related to monitoring the state of people. Presented in the art, for example, are bed sensors with which the presence of a person in bed can be measured by means of a pressure sensor that is placed on the bed in such a way that it detects the weight of a person when the person is lying in bed.

Also known in the art is to use sensors to be installed on the floor, or under it, that detect the presence and movements of people by means of capacitive sensors or sensors based on pressure, and by means of this data to deduce whether a person needing monitoring is in bed or has gone somewhere else.

Not presented in the art, however, is a type of sensor that could reliably measure with one and the same sensor the presence of a person in bed, his/her departure from the bed and whether the bed has become wet, e.g. as a consequence of sweating, urine or other secretion.

BRIEF DESCRIPTION OF THE INVENTION

The invention presents a sensor arrangement, by means of which a person on a base, such as in a bed or on a seat, can be monitored. The sensor arrangement according to the invention comprises measuring electronics and a sensor that can be fitted onto the base, e.g. onto a bed or a seat.

In the solution according to the invention by means of a sensor being installed on a base, the presence of a person on the base, and whether the base, such as a bed or seat, has become wet, can be detected. The arrangement according to the invention is adapted to determine, by means of the data measured by the measuring electronics and the sensor, the wetting of a base on the basis of measurement based on a change in moisture. By means of the solution of the invention the presence of a person on a base can be determined in the solution according to the invention e.g. by measuring the effect of the presence of a person on the electrical conductivity of the immediate surroundings of the sensor by means of capacitance measurement, by means of a change in measured moisture and/or by measuring the pressure being exerted on the sensor e.g. with a sensor measuring pressure.

The arrangement according to the invention can further comprise a data processing device, suited to processing sensor observations, comprising a processor and a memory.

One application of the solution of the invention is the monitoring of the condition and state of elderly people in beds or on seats, e.g. in their homes, in retirement homes or in hospitals. The information collected by the system can be sent e.g. to a central control room or to a corresponding body that supervises a certain area and/or the people in it.

By using the method according to claim 1 and the system according to claim 10, the problems of the state of the art can be eliminated and an arrangement can be implemented that corresponds to the requirements according to usage needs. The invention is characterized by what is disclosed in the claims below.

One advantage, among others, in the arrangement according to the invention compared to earlier systems is that by means of it the presence of a person on a base, such as in bed, his/her departure from the base and whether the base has become wet, e.g. as a consequence of sweating, urine or other secretion, can be reliably measured with a single sensor.

BRIEF DESCRIPTION OF THE FIGURES

The invention is illustrated with the following drawings, of which

DETAILED DESCRIPTION OF THE INVENTION

Figure 1:
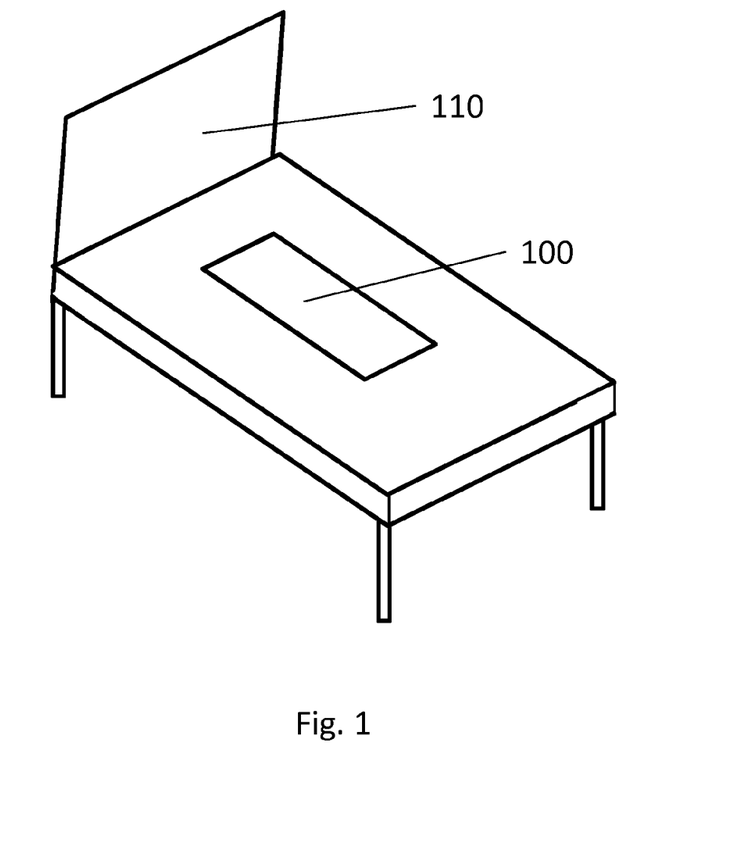
FIG. 1 presents a sensor arrangement according to one embodiment of the invention, the arrangement being fitted onto a bed.

FIG. 1 presents an embodiment of a sensor arrangement according to the invention, the embodiment presenting a base on which a sensor structure 100 according to the arrangement of the invention is fitted. In the case of this embodiment, the base is a bed 110. The base can also be e.g. a seat, such as a chair, an armchair or a sofa. In the arrangement according to the invention by means of the sensor structure the presence of a person on the base and whether the base has become wet can be determined. The sensor structure to be used in the invention can comprise a sensor measuring moisture or a change in moisture. The sensor structure to be used in the invention can also comprise an arrangement by means of which the effect of the presence of a person on the electrical conductivity of the immediate surroundings of the sensor can be measured. The sensor structure according to the invention can also, in one embodiment of the invention, comprise a sensor measuring pressure. A sensor measuring moisture or a change in moisture, a sensor measuring the effect of presence on electrical conductivity and/or a sensor measuring pressure can be integrated into the same sensor structure.

The arrangement according to the invention further comprises measuring electronics, and the arrangement is adapted to determine, by means of the data measured by the measuring electronics and the sensor structure, the moisture level and a change in the moisture level in an area of the sensor structure, e.g. in the whole area of the sensor structure or in only a part of the area of the sensor structure. On the basis of the moisture level, or a change in it, the arrangement can determine whether a base, such as e.g. a bed, has become wet.

The solution according to the invention can also determine, by means of the data measured by the measuring electronics and the sensor, the presence of a person on the base and his/her departure from the base. The presence of a person can be determined by means of a measurement based on pressure, a measurement based on an increase in electrical conductivity caused by a presence occurring near a sensor of the torso of the person, or a measurement based on measuring moisture. In one embodiment of the invention combinations of the aforementioned technologies can be used for determining presence.

The measuring electronics can be integrated into the sensor structure or it can be a separate unit, which is connected to the sensor structure by means of a wired or wireless connection. There can be a wired or wireless connection from the measuring unit, with which connection the measured data can be transmitted onwards.

In the solution according to the invention the moisture level can be measured and the measured moisture level is recorded as a comparison moisture level value when it is detected that a person has come onto the base. The measured moisture level is compared to the recorded comparison value for moisture level and the system can deduce by means of this e.g. whether a person is on the base, whether the person has left the base and whether the base has become wet. If the measured moisture level is lower than the recorded comparison value for moisture level, the arrangement can determine that the person has got out of bed and/or departed from the base. If the measured moisture level is higher than the recorded comparison value for moisture level, the arrangement can determine that the base, such as a bed, has become wet. The base might become wet e.g. as a consequence of sweating or urinating. In both cases this information facilitates the care of a person that is e.g. in bed. Sweating, for example, can indicate that the person has a fever or some corresponding problem.

The sensor structure to be used in the arrangement of the invention can be e.g. such in size and shape that it covers the area of the back and/or pelvis, in which case by means of it a moisture level that is raised both by urinating and sweating can be detected. The sensor structure of the invention can extend, when installed into position, e.g. from the back part of a person in bed to his/her groin area.

In one embodiment of the invention wherein moisture is measured as well as the pressure being exerted on the sensor structure, the moisture measurement can be performed in a different location than the measurement of the pressure being exerted on the sensor structure. In this case the sensor areas for moisture measurement can be in a different part of the sensor structure than the sensor areas measuring pressure. In one embodiment of the invention the parts measuring the moisture of the sensor structure and the parts measuring pressure are located in the same area, e.g. in essentially the whole area of the sensor structure.

In one embodiment of the invention the location in the area of the sensor structure of a detected higher moisture level can be determined and, on the basis of the location, the arrangement can further deduce that if the moisture occurs in a part of the sensor structure coming below the back, the moisture is sweat and if the moisture appears at the bottom end of the sensor at the point of the bottom end of a person, the moisture is urine or some other secretion.

An increase in electrical conductivity in the immediate surroundings caused by moisture, an indentation or the presence of a person's torso can be measured in the arrangement according to the invention continuously or, alternatively, at certain fixed or variable intervals of time. It is also possible to change the measuring function in such a way that a change is effected from the continuous measuring method to a measuring method in which the measuring is performed at certain time intervals, and/or vice versa.

The system according to the invention can assess the measurement results of the sensor and on the basis of the measurement results can perform certain procedures, such as e.g. control functions and alarm functions. The arrangement can also comprise a memory means, in which the system is adapted to record sensor data, or information derived from it, for observing the chronological dependency of the behavior of a person. The measurement results of the sensor, or the information derived from them, can be transmitted onwards using a wired or wireless telecommunications connection.

The information collected by the system can be sent e.g. to a control center or to another body that supervises the area and/or the people therein. The transfer of information between the system and some recipient can be performed using a phone connection, a wired broadband connection, wireless connections, or an optical or acoustic connection. It is advantageous in the data transfer to take into account issues relating to data security and privacy, which many official regulations also address. The data transfer can be effected e.g. by an action of the central unit of the system. The central unit can comprise a processor and a memory, and it can be e.g. a data processing device. The central unit of the system can manage one or more sensors. The central unit can be integrated into the sensors or they can be disposed separately or in separate units.

It is possible that some of the functions of the central unit are performed elsewhere via a data network connection, e.g. in a central control room or service center.

The system can also control the functions of the area to be monitored, such as the lighting, air-conditioning, access control, locking, and other alarm systems, control systems and monitoring systems, or robotic devices that are in the area. One example of this kind of control function is that the lighting can be switched on at night when the arrangement detects that a person has got out of bed. In this case the system comprises the means needed for this, such as e.g. Bluetooth means, WLAN means or other such transmitter-receiver means.

Figure 2:
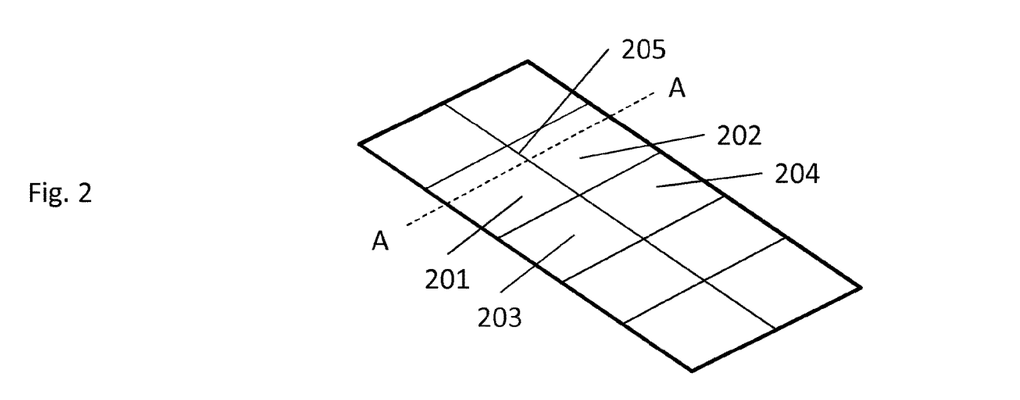
FIG. 2 presents a sensor structure according to an embodiment of the invention.

FIG. 2 presents a sensor structure according to one embodiment of the invention, which is composed of electrically conductive areas 201, 202, 203, 204 that are one beside another and insulated from each other. The electrically conductive areas are insulated from each other with insulation 205.

Figure 3:
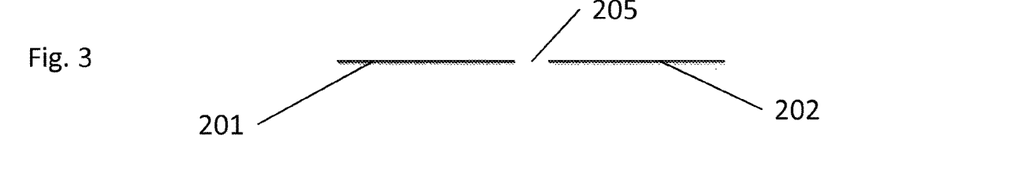
FIG. 3 presents a cross-section of a sensor structure according to an embodiment of the invention.

FIG. 3 presents a cross-section of one embodiment of the sensor structure of FIG. 2, by means of which the moisture level, a change in the moisture level and/or a presence can be measured. In the embodiment of FIG. 3 the sensor structure comprises at least two electrically conductive parts 201,202 that are insulated from each other. The electrically conductive areas, e.g. electrodes, 201, 202 can be e.g. copper sheets. The arrangement according to the invention is adapted to determine the moisture level by measuring the capacitance and/or resistance between the electrically conductive areas 201, 202. Two electrically conductive areas that are insulated from each other can be on the same plane. When moisture comes onto the surface of the sensor structure, the capacitance and/or resistance between the electrically conductive areas 201 and 202 change(s) because the moisture conducts electricity over the insulating part 205 dividing the areas. The electrically conductive areas of the sensor structure must be insulated with insulating material from the person being measured that is on top of the sensor structure. A material, such as cloth, that insulates electricity but is permeable to moisture can be used as this type of insulating material.

In one embodiment of the invention with the sensor structure according to FIG. 3 an increase in electrical conductivity caused by the presence of a person's torso can also be measured and, by means of this, the presence of a person can be determined. The presence of a person's torso increases the electrical conductivity of the immediate surroundings of the sensor and therefore changes the capacitance between the electrically conductive areas 201, 202. In this embodiment the capacitance is measured when the person being monitored has placed himself/herself onto a base, e.g. a bed. If changes in capacitance occur after this, this is a consequence of an increase in liquid because liquid changes the capacitance, or it is a consequence of the person getting out of bed.

Figure 4:
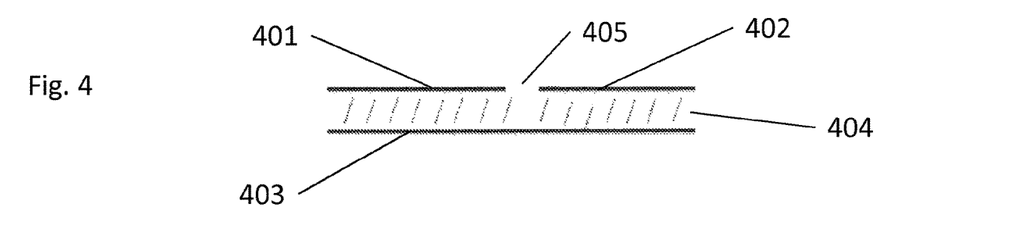
FIG. 4 presents a cross-section of a sensor structure according to an embodiment of the invention.

FIG. 4 presents a cross-section of one embodiment of the sensor structure of FIG. 2, by means of which the moisture level and pressure are measured. The sensor of FIG. 4 comprises at least three electrically conductive areas 401, 402, and 403 that are insulated from each other. The electrically conductive areas 401 and 402 are on the same plane as each other and the electrically conductive area 403 is situated below them. The electrically conductive areas can be e.g. copper sheet. The arrangement is adapted to determine the moisture level by measuring the capacitance and/or resistance between the first 401 and the second 402 electrically conductive areas in the same manner as in the embodiment of FIG. 3. In the case of the sensor structure according to this embodiment of the invention, as also in the embodiment presented in FIG. 3, when moisture comes onto the surface of the sensor structure, the capacitance between the electrically conductive areas 401 and 402 changes because the moisture conducts electricity over the insulating part 405 dividing the different areas.

The sensor structure according to the embodiment presented in FIG. 4, in addition to this, determines presence also by means of pressure identification, by measuring the capacitance between the first 401 and the third 403 electrically conductive areas and/or between the second 402 and the third 403 electrically conductive areas. Between the upper layer formed from the first 401 and second 402 electrically conductive areas and the lower layer formed from the third electrically conductive area 403 is an electrically insulating material 404.

In the solution of this embodiment of the invention, the presence of a person in bed can be determined with the sensor measuring moisture described above and, in addition to this, with pressure measurement. It is also possible to use only a pressure sensor for determining presence. One advantage of this embodiment is that by means of it the wetting of the bed and the presence of a person in bed can be detected more reliably. The operation of the capacitive pressure sensor of the sensor structure is based on the capacitance between the sensor electrodes formed from the electrically conductive areas 401, 402, 403 changing when the distance between them changes when the sensor is compressed. When pressure is exerted on the sensor the electrically conductive areas 401 and 403, and also 402 and 403, approach each other, in which case the capacitance between them changes.

Figure 5:
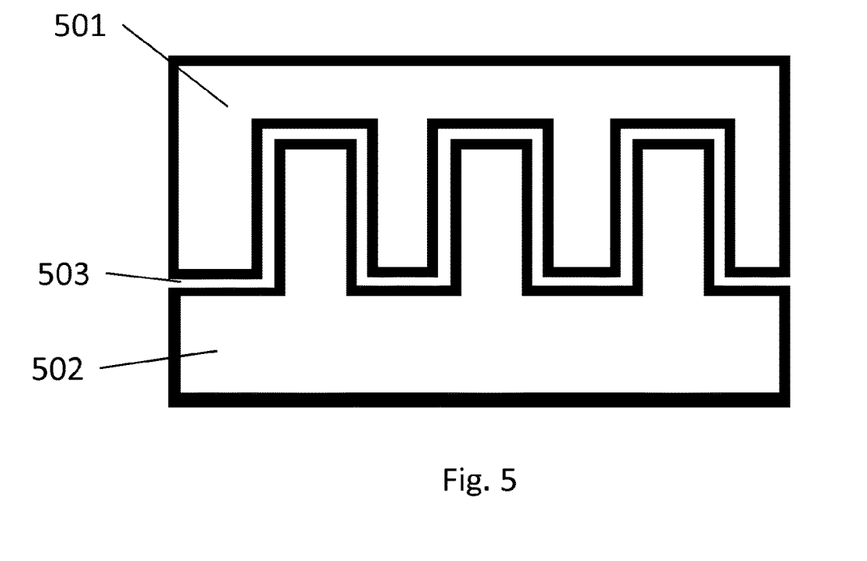
FIG. 5 presents the construction of a sensor structure according to an embodiment of the invention.

FIG. 5 presents one embodiment of the invention, in which the electrically conductive areas of the sensor structure are formed to be tooth-shaped. By means of this embodiment the presence of a person and moisture can be measured. The operating principle of the sensor according to FIG. 5 is similar to that of the embodiment presented in FIG. 3. A difference to the embodiment presented in FIGS. 2 and 3 is that with the sensor according to FIG. 5 only two separate electrically conductive areas 501, 502 i.e. electrodes, and the area 503 electrically insulating them from each other are needed for the reliable measurement of an extensive area. In this case determination of the location of the moisture is not possible. In one embodiment of the invention the sensor structure according to the invention can comprise a number of sensors according to FIG. 5.

The system according to the invention can also be used alongside a system based on floor sensors and the control and management of the systems can be implemented by action of the same devices and softwares.

The invention thus relates to a sensor arrangement, which comprises measuring electronics and a sensor structure 100 that can be fitted onto a base 110. The sensor structure 100 comprises at least one sensor, and the arrangement is adapted to determine, by means of the data measured by the measuring electronics and the sensor, whether the moisture of the base has changed. The arrangement is further adapted to determine, on the basis of the data measured by the measuring electronics and the sensor, the presence of a person on the base.

In one embodiment of the invention the base is a bed and/or seat, such as an armchair, sofa or chair.

In one embodiment of the invention the sensor comprises at least two electrodes 201,202; 401,402; 501,502 insulated from each other.

In one embodiment of the invention the sensor arrangement is adapted to determine a change in the moisture of the base by measuring the resistance between the electrodes and by comparing it to a reference value that has been measured and recorded when the base was dry.

In one embodiment of the invention the sensor arrangement is adapted to determine a presence by measuring the capacitance between the electrodes and by comparing it to a reference value that has been measured and recorded when the base was empty.

In one embodiment of the invention the sensor arrangement is adapted to determine a change in the moisture of the base by measuring the capacitance between the electrodes and by comparing it to a reference value that has been measured and recorded after the presence started when the base was dry.

In one embodiment of the invention the sensor arrangement is adapted to detect a force exerted by a person on the sensor and to detect presence by measuring the force being exerted on the sensor, and by comparing said force to a reference value that has been measured and recorded when the base was empty.

In one embodiment of the invention the sensor comprises at least two planar electrodes 401,403; 402,403 disposed one on top of the other, between which is a compressible insulation 404, and the sensor arrangement is adapted to measure the force being exerted on the sensor by measuring the capacitance between the electrodes 401,403; 402,403.

In one embodiment of the invention the sensor comprises piezoelectric material, and the sensor arrangement is adapted to measure the force being exerted on the sensor by measuring voltage fluctuations in the sensor that are caused by a piezoelectric phenomenon.

In one embodiment of the invention the sensor is adapted to react with a change in resistance to a force exerted on it, and the sensor arrangement is adapted to measure the force being exerted on the sensor by measuring resistance fluctuations in the sensor.

In one embodiment of the invention the sensor comprises a strain gauge and/or piezoresistive element.

In one embodiment of the invention the electrodes detecting a change in moisture are in the same sensor structure as the structure detecting the force exerted on the sensor by a person.

In one embodiment of the invention the sensor of the sensor arrangement comprises at least three electrically conductive areas 401, 402, 403 that are insulated from each other, e.g. copper sheets, which are arranged in such a way that the arrangement is adapted to determine the moisture level by measuring the capacitance and/or resistance between the first 401 and the second 402 electrically conductive areas and to determine a presence by means of the force exerted on a sensor by measuring the capacitance between the first 401 and the third 403 electrically conductive areas and/or between the second 402 and the third 403 electrically conductive areas.

In one embodiment of the invention the sensor arrangement is adapted to assess the measurement results of the sensor and on the basis of the measurement results to perform certain procedures, such as e.g. control functions and alarm functions.

In one embodiment of the invention the sensor arrangement comprises a memory means, in which it is adapted to record sensor data, or information derived from it, for observing the chronological dependency of the behavior of a person.

In one embodiment of the invention the sensor arrangement comprises means for transmitting the measurement results of the sensor, or the information derived from them, onwards using a wired or wireless telecommunications connection.

The invention thus relates to a method for monitoring with a sensor arrangement a person on a base, which arrangement comprises measuring electronics and a sensor structure 100 that can be fitted onto the base. The sensor structure 100 comprises at least one sensor, and in the method, by means of the data measured by the measuring electronics and the sensor, it is determined whether the moisture of the base has changed and the presence of a person on the base is further determined In one embodiment of the invention by means of the presence data also the arrival on a base, departure from the base, staying on the base and/or staying off the base of a person is detected by examining the presence data as a function of time.

In one embodiment of the invention the sensor comprises at least two electrodes 201,202;401,402;501,502 insulated from each other and in the method the resistance between the electrodes is measured, the measurement result is compared to a reference value that has been measured and recorded when the base was empty, and the wetting of the base is detected if the measured resistance is lower than the reference value.

In one embodiment of the invention the sensor comprises at least two electrodes 201,202;401,402;501,502 insulated from each other and in the method the capacitance between the electrodes is measured, the measurement result is compared to a reference value that has been measured and recorded when the base was empty, and the presence of a person is detected if the measured capacitance is higher than the reference value.

In one embodiment of the invention wetting of the base is detected if the measured capacitance is higher than the reference value that has been measured and recorded after a presence had started when the base was dry.

In one embodiment of the invention the sensor comprises means for measuring the force being exerted on the sensor by a person, and in the method the force being exerted on the sensor is measured, is compared to a reference value that has been measured and recorded when the base was empty, and the presence of a person is detected if the force is greater than the reference value.

In one embodiment of the invention the sensor comprises at least two planar electrodes 401,403; 402,403 disposed one on top of the other, between which is a compressible insulation 404, and in the method the force being exerted on the sensor is measured by measuring the capacitance between the electrodes 401,403; 402,403.

In one embodiment of the invention the sensor comprises piezoelectric material, and in the method the force being exerted on the sensor is measured by measuring voltage fluctuations in the sensor that are caused by a piezoelectric phenomenon.

In one embodiment of the invention the resistance of the sensor changes as a consequence of a force exerted on it, and in the method the force being exerted on the sensor is measured by measuring the resistance of the sensor.

In one embodiment of the invention the sensor comprises a strain gauge and/or piezoresistive element and in the method the force being exerted on the sensor is measured by measuring the resistance of the strain gauge and/or of the piezoresistive element.

In one embodiment of the invention the sensor comprises at least three electrically conductive areas 401, 402, 403 that are insulated from each other, e.g. copper sheets, which are arranged in such a way that the moisture level is determined by measuring the capacitance and/or resistance between the first 401 and the second 402 electrically conductive areas, and the force exerted on the sensor by determining the capacitance between the first 401 and the third 403 electrically conductive areas and/or between the second 402 and the third 403 electrically conductive areas.

In one embodiment of the invention the information derived on the basis of the measurement results of the sensor is assessed with criteria that are either fixed, preset or adjustable, and guided by the results of the assessment certain procedures, such as e.g. control functions and alarm functions, are performed.

In one embodiment of the invention the arrangement comprises a memory means, in which is recorded sensor data, or information derived from it, for observing the chronological dependency of the behavior of a person.

In one embodiment of the invention the measurement results of the sensor, or the information derived from them, are transmitted onwards using a wired or wireless telecommunications connection.

It is obvious to the person skilled in the art that the different embodiments of the invention are not limited solely to the examples described above, and that they may therefore be varied within the scope of the claims presented below. The characteristic features possibly presented in the description in conjunction with other characteristic features can also, if necessary, be used separately to each other.

The invention claimed is:

1. A sensor arrangement, comprising:
   a base;
   a first electrically conductive plate on the base;
   a plurality of second electrically conductive plates parallel to the first conductive plate;
   a first electrically insulative material between the first electrically conductive plate and the plurality of second electrically conductive plates;

a second electrically insulative material between the plurality of second electrically conductive plates, the second electrically insulative material being permeable to moisture, wherein the sensor arrangement is adapted to determine whether the moisture of the base has changed by changes in an electrical characteristic between two of the plurality of second electrically conductive plates, and the sensor arrangement is further adapted to determine pressure on the base by changes in an electrical characteristic between the first electrically conductive plate and one of the plurality of second electrically conductive plates.

2. The sensor arrangement according to claim 1, wherein the base is a bed or a seat.

3. The sensor arrangement according to claim 1, wherein the sensor arrangement is adapted to determine a change in the moisture by measuring a resistance between the two of the plurality of second electrically conductive plates and by comparing the resistance to a reference value that has been measured and recorded when the base was dry.

4. The sensor arrangement according to claim 1, wherein the sensor arrangement is adapted to determine the pressure by measuring a capacitance between the first electrically conductive plate and one of the plurality of second electrically conductive plates and by comparing the capacitance to a reference value that has been measured and recorded when the base was empty.

5. The sensor arrangement according to claim 1, wherein the sensor arrangement is adapted to determine a change in the moisture of the base by measuring a capacitance between the two of the plurality of second electrically conductive plates and by comparing the capacitance to a reference value that has been measured and recorded after a presence had started when the base was dry.

6. The sensor arrangement according to claim 1, further comprising a piezoelectric material, and the sensor arrangement is adapted to measure the pressure by measuring voltage fluctuations in the sensor that are caused by a piezoelectric phenomenon.

7. The sensor arrangement according to claim 1, wherein the sensor arrangement is adapted to react with a change in resistance, and the sensor arrangement is adapted to measure a force being exerted on the sensor arrangement by measuring resistance fluctuations.

8. The sensor arrangement according to claim 7, further comprising a strain gauge or a piezoresistive element.

9. The sensor arrangement according to claim 1, further comprising a memory, the memory adapted to record sensor data, or information derived from the sensor data, for observing the chronological dependency of the behavior of a person.

10. The sensor arrangement according to claim 1, further comprising a transmitter for transmitting measurements, or the information derived from the measurements, using a wired or wireless telecommunications connection.

11. A method for monitoring a person with a sensor arrangement, comprising:
forming a first electrically conductive plate on a base;
forming a plurality of second electrically conductive plates parallel to the first conductive plate;
forming a first electrically insulative material between the first electrically conductive plate and the plurality of second electrically conductive plates;
forming a second electrically insulative material between the plurality of second electrically conductive plates, the second electrically insulative material being permeable to moisture;
determining whether moisture of the base has changed by changes in an electrical characteristic between two of the plurality of second electrically conductive plates; and
determining pressure on the base by changes in an electrical characteristic between the first electrically conductive plate and one of the plurality of second electrically conductive plates.

12. The method according to claim 11, wherein the base is a bed or a seat.

13. The method according to claim 11, wherein by measuring presence data, arrival on a base, departure from the base, staying on the base and/or staying off the base of a person is detected by examining the presence data as a function of time.

14. The method according to claim 11, wherein determining whether the moisture of the base has changed comprises measuring resistance between the two of the plurality of second electrically conductive plates, and comparing the measured resistance a reference value that has been measured and recorded when the base was dry, and detecting wetting of the base if the measured resistance is lower than the reference value.

15. The method according to claim 11, wherein determining pressure on the base comprises measuring capacitance between the first electrically conductive plate and one of the plurality of second electrically conductive plates, and comparing the measured capacitance to a reference value that has been measured and recorded when the base was empty, and detecting the presence of a person on the base if the measured capacitance is higher than the reference value.

16. The method according to claim 15, wherein determining whether the moisture of the base has changed comprises comparing a measured capacitance between the two of the plurality of second electrically conductive plates to a reference value that has been measured and recorded after a presence had started when the base was dry.

17. The method according to claim 11, determining pressure on the base comprises comparing a measured pressure to a reference value that has been measured and recorded when the base was empty, and the presence of a person is detected if the pressure is greater than the reference value.

18. The method according to claim 17, further comprising a piezoelectric material, and
wherein determining pressure on the base comprises measuring voltage fluctuations that are caused by a piezoelectric phenomenon.

19. The method according to claim 17, wherein by determining pressure on the base comprises measuring a resistance between the first electrically conductive plate and one of the plurality of second electrically conductive plates.

20. The method according to claim 19, wherein the sensor comprises a strain gauge and/or a piezoresistive element, and
wherein determining pressure on the base comprises measuring a resistance of the strain gauge and/or of the piezoresistive element.

21. The method according to claim 11, wherein the information derived on the basis of the measurements is assessed with criteria that are either fixed, preset or adjustable.

22. The method according to claim 11, wherein the arrangement comprises a memory, in which is recorded sensor data, or information derived from it, for observing the chronological dependency of the behavior of a person.

23. The method according to claim 11, wherein measurements, or the information derived from them, are transmitted using a wired or wireless telecommunications connection.

* * * * *